United States Patent
Scherlen et al.

(10) Patent No.: US 9,282,886 B2
(45) Date of Patent: Mar. 15, 2016

(54) DEVICE FOR DETERMINING A GROUP OF VISION AIDS SUITABLE FOR A PERSON

(75) Inventors: Anne-Catherine Scherlen, Charenton le Pont (FR); Pascal Voillemin, Charenton le Pont (FR)

(73) Assignee: ESSILOR INTERNATIONAL (COMPAGNIE GENERALE D'OPTIQUE), Charenton Le Pont (FR)

( * ) Notice: Subject to any disclaimer, the term of this patent is extended or adjusted under 35 U.S.C. 154(b) by 95 days.

(21) Appl. No.: 14/237,628

(22) PCT Filed: Aug. 9, 2011

(86) PCT No.: PCT/FR2011/000462
§ 371 (c)(1),
(2), (4) Date: Mar. 11, 2014

(87) PCT Pub. No.: WO2013/021102
PCT Pub. Date: Feb. 14, 2013

(65) Prior Publication Data
US 2014/0211166 A1   Jul. 31, 2014

(51) Int. Cl.
*A61B 3/02* (2006.01)
*A61B 3/10* (2006.01)
*A61B 3/032* (2006.01)
*A61B 3/00* (2006.01)
*A61B 3/024* (2006.01)
*A61B 3/06* (2006.01)
*A61B 3/08* (2006.01)
*A61B 3/113* (2006.01)

(52) U.S. Cl.
CPC . *A61B 3/032* (2013.01); *A61B 3/02* (2013.01); *A61B 3/005* (2013.01); *A61B 3/0033* (2013.01); *A61B 3/022* (2013.01); *A61B 3/024* (2013.01); *A61B 3/063* (2013.01); *A61B 3/066* (2013.01); *A61B 3/08* (2013.01); *A61B 3/113* (2013.01)

(58) Field of Classification Search
USPC .................................................. 351/200–246
See application file for complete search history.

(56) References Cited

U.S. PATENT DOCUMENTS

| 6,045,225 | A | 4/2000 | Hosoi | |
| 6,386,707 | B1 * | 5/2002 | Pellicano | 351/246 |
| 6,533,418 | B1 * | 3/2003 | Izumitani et al. | 351/204 |

(Continued)

FOREIGN PATENT DOCUMENTS

| EP | 1 336 924 | 8/2003 |
| EP | 1 892 660 | 2/2008 |

(Continued)

OTHER PUBLICATIONS

International Search Report dated Apr. 24, 2012, corresponding to PCT/FR2011/000462.

(Continued)

*Primary Examiner* — Mohammed Hasan
(74) *Attorney, Agent, or Firm* — Young & Thompson

(57) ABSTRACT

A device (10) for determining a group of at least one vision aid apparatus suitable for the vision of an individual, includes computing elements programmed to: a) determine at least one characteristic of the vision of the individual, b) determine at least one use of the group of at least one vision aid apparatus, desired by the individual, c) determine the group of at least one vision aid apparatus as a function of the characteristic of the vision and of the use desired by the individual.

14 Claims, 2 Drawing Sheets

(56) References Cited

U.S. PATENT DOCUMENTS

| | | |
|---|---|---|
| 6,792,401 B1 * | 9/2004 | Nigro et al. .................. 703/6 |
| 6,944,327 B1 * | 9/2005 | Soatto ...................... 382/154 |
| 7,222,091 B2 | 5/2007 | Yoshida |
| 7,374,285 B2 * | 5/2008 | Toshima et al. ............ 351/205 |
| 7,524,065 B1 * | 4/2009 | Ogilvie ...................... 351/222 |
| 2004/0174499 A1 | 9/2004 | Toshima et al. |

FOREIGN PATENT DOCUMENTS

| | | |
|---|---|---|
| JP | 02-307425 | 12/1990 |
| JP | 09-96784 | 4/1997 |
| JP | 10-216090 | 8/1998 |
| WO | 01/34020 | 5/2001 |
| WO | 2006/010611 | 2/2006 |
| WO | 2008/089995 | 7/2008 |

OTHER PUBLICATIONS

Japanese Office Action, dated Jun. 16, 2015, in corresponding Japanese Patent Application No. 2014-524425.

* cited by examiner

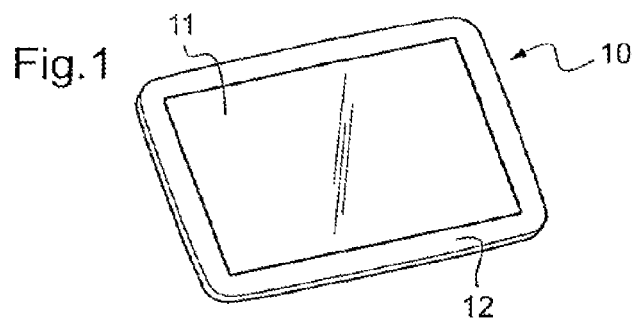
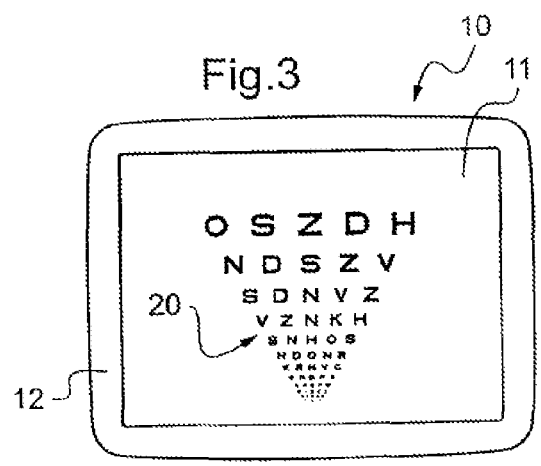
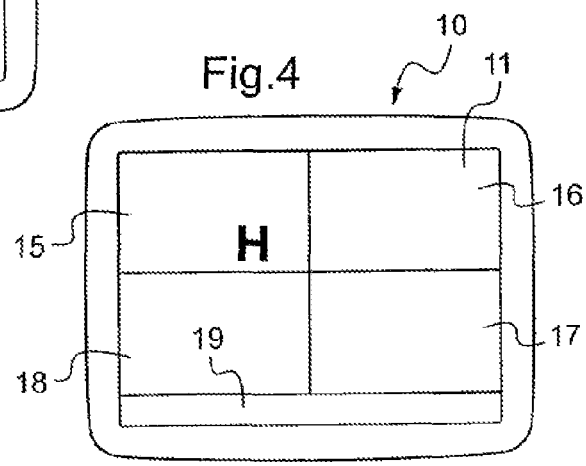

DEVICE FOR DETERMINING A GROUP OF VISION AIDS SUITABLE FOR A PERSON

TECHNICAL FIELD TO WHICH THE INVENTION PERTAINS

The present invention relates to a device for determining a group of at least one vision aid apparatus suitable for the vision of an individual.

PRIOR ART

There exist very many vision aid apparatuses exhibiting extremely different characteristics, both from the point of view of the type of aid to vision afforded, for example improvement in visual acuity, contrast, or decrease in glare, and from the point of view of the type of possible uses of this apparatus, for example use indoors or outdoors, use for reading, for writing, for distance viewing, etc.

Thus the determination of one or more visual apparatus best suitable for an individual as a function of his vision and of the use that he desires to make of the apparatus currently requires a process that is relatively lengthy and arduous both for the optician and for the individual.

SUBJECT OF THE INVENTION

In order to remedy the aforementioned drawback of the prior art, the present invention proposes a device making it possible to determine simply and effectively at least one apparatus specifically suitable for the needs and desires of an individual.

More particularly, there is proposed according to the invention a device for determining a group of at least one vision aid apparatus suitable for the vision of an individual, comprising computing means programmed to:

a) determine at least one characteristic of the vision of said individual, b) determine at least one use of the group of at least one vision aid apparatus, desired by the individual, c) determine said group of at least one vision aid apparatus as a function of the characteristic of the vision and of the use desired by the individual.

Thus, one and the same device is suitable, on the one hand, for performing the individual's vision tests making it possible to precisely determine the technical characteristics of the apparatus suitable for improving the vision of the individual and, on the other hand, for recording the desires of the individual in regard to use of the apparatus.

Vision tests is here intended to mean tests aimed at determining the optical, physical, mechanical, physiological or nervous operating characteristics of the individual's eyes.

Use of the apparatus is here intended to mean either the activities desired by the user, for example reading or distance viewing or else the conditions of use of the apparatus, for example having one's hands free, using the apparatus for long durations etc.

Finally, the device according to the invention is programmed to select a group of apparatus suitable for the individual by cross-referencing the two types of information gathered.

The following are other nonlimiting and advantageous features of the device according to the invention:

in step a), at least one of the following characteristics of the vision of the individual is determined: visual acuity, reading acuity, sensitivity to contrast, extent of the field of vision, glare, oculomotricity, eye-hand coordination, color vision, stereoscopy;

it comprises a display part and, in step a), the characteristic of the vision of the individual is determined by virtue of a test of recognition of an image displayed on said display part;

in step a), several characteristics of the vision of the individual are determined successively and the content and/or the sequencing of the subsequent tests of the vision is suitable as a function of the results of the previous tests;

in step b), at least one of the following uses desired by the individual is determined: reading, writing, near vision, far vision, watching television, working on an object situated at an intermediate distance;

in step b), the device records, for each desired use, an index of importance of this use for the individual;

in step b), at least one ergonomic condition desired by the individual for the desired use is recorded, from among the following ergonomic conditions: use indoors, use outdoors, standard ergonomic distance of use, long or short duration of use;

in step c), the computing means comprise in memory a pre-established list of vision aid apparatuses and are programmed to preselect, in the course of a step c1), from among this pre-established list, a set of vision aid apparatuses suitable for aiding the individual as a function of at least one characteristic of his vision determined in step a);

in step c), the computing means are programmed to select in a step c2), from among said set of vision aid apparatuses, a subset of vision aid apparatuses exhibiting the ergonomic conditions of use desired by the individual;

in step c), the computing means are programmed to select in a step c3), from among said subset of vision aid apparatuses that is determined in step c2), a subset of vision aid apparatuses that is most suitable for the uses desired by the individual;

the list of vision aid apparatuses takes the form of an electronic register, each record of which comprises:

an identifier of each vision aid apparatus, first performance indices dependent on the aid afforded by this apparatus for all the possible vision characteristics of the individual and second performance indices dependent on the suitability of this apparatus for all possible uses;

each record of the electronic register furthermore comprises an indicator of at least one ergonomic condition of use of the corresponding apparatus;

in step c1), the computing means are programmed to preselect from said register the set of vision aid apparatuses for which at least one of said first indices corresponds to the associated vision characteristic of the individual, in step c2), the computing means are programmed to select from said set determined in step c1), the subset of vision aid apparatuses for which at least one indicator of the ergonomic conditions of use of the apparatus corresponds to the condition of use desired by the individual, and, in step c3), the computing means are programmed to select, from said set determined in step c2), the subset of vision aid apparatuses for which the second index is greater than a threshold value for at least one use desired by the individual.

DETAILED DESCRIPTION OF AN EXEMPLARY EMBODIMENT

The following description, given with regard to the appended drawings, by way of nonlimiting example, will allow what the invention consists of and how it can be carried out to be understood.

In the appended drawings:

FIG. 1 is a schematic view of the device according to the invention,

FIG. 3 is a schematic representation of a visual acuity test displayed on the device of FIG. 1, FIG. 4 is a schematic representation of a contrast test displayed on the device of FIG. 1.

Figure 2:
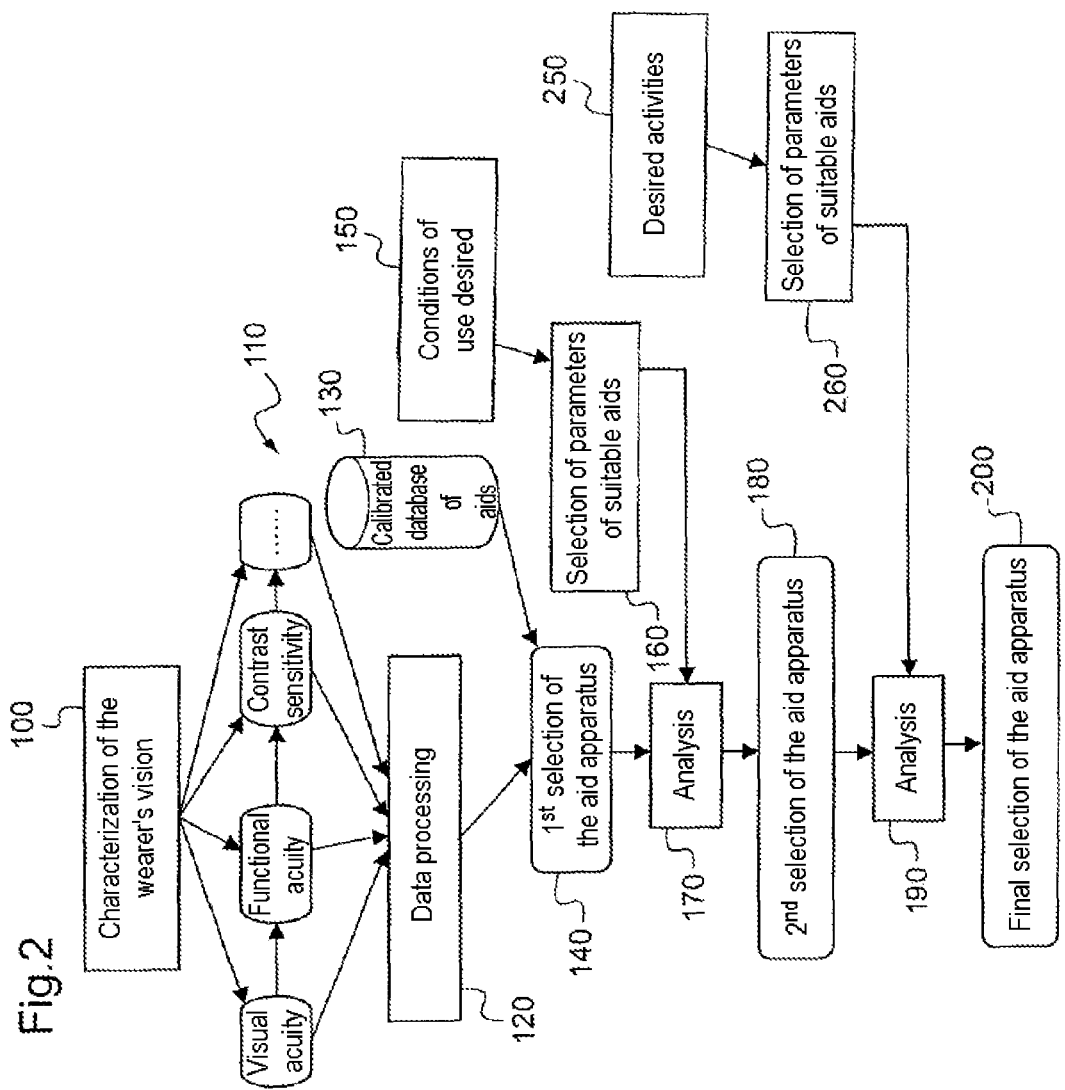
FIG. 2 is a schematic view of a possible mode of operation of the device of FIG. 1.

The device for determining a group of at least one visual apparatus according to the invention can be used for any individual, whatever the characteristics of their vision.

It can for example make it possible to determine whether the apparatus most suitable for an individual forms part of the group of the spectacles furnished with single focus, dual focus or progressive corrective lenses.

However, this device is particularly advantageous for determining a group of apparatuses intended to aid a partially-sighted person.

Indeed, the vision of partially-sighted people can be impaired by very many factors. These may involve for example a decline in visual acuity, a decrease in the perception of contrasts or colors, a decrease in the motricity and/or field of vision of this person's eyes.

Furthermore, the impairment of the vision of these people being particularly significant, it is not always possible to offer them a vision aid apparatus suitable for use in all situations.

The device according to the invention then makes it possible in a simple and fast manner to evaluate various aspects of the vision of the individual as well as the uses envisaged by the individual of the vision aid apparatus, so as finally to select a group of apparatuses achieving the best compromise between the technical characteristics necessary for correcting the individual's vision defects and the ergonomic and practical characteristics necessary for the uses envisaged as a priority by this individual.

More precisely, there exist several hundred vision aid apparatuses for partially-sighted people exhibiting different technical, ergonomic and practical characteristics.

As a whole, vision aid apparatuses can be segmented into seven groups of vision aid apparatus:
- magnifying glasses,
- microscopic spectacles (or high-power spectacles),
- Galilean and Keplerian telescopic systems,
- portable electronic aids,
- electronic aids of the TV-magnifier type,
- lamps,
- filters.

In FIG. 1 is represented a possible exemplary embodiment for the device according to the invention.

This device here takes the form of a tactile tablet 10 comprising a tactile display screen 11 and a frame 12 surrounding it.

This tablet 10 can be held by the individual whose vision is evaluated, placed on a table or integrated into a more complex machine.

The tablet 10 comprises computing means as well as means for determining at least one characteristic of the vision of said individual in a step a) (block 100 of FIG. 2), means for determining at least one use, desired by the individual, of the group of vision aid apparatuses in a step b) (block 150 of FIG. 2), means for determining said group of vision aid apparatuses as a function of the characteristic of the vision and of the use desired by the individual in a step c) (block 180 of FIG. 2).

The computing means are programmed to control the aforementioned means.

The general operation of this device is represented schematically in FIG. 2.

In step a) represented by the block 100 of FIG. 2, the device according to the invention characterizes the wearer's vision. Accordingly, a series of tests represented by the blocks 110 are carried out by virtue of the device 10.

The results of these tests are processed by the computing means for determining the optical characteristics of the apparatus suitable for the tested individual (block 120 of FIG. 2).

Thereafter, these optical characteristics are compared (block 140 of FIG. 2) against the characteristics of the available apparatuses which are grouped together in a database 130 so as to select a first set of suitable apparatuses (step c1)).

In step b) represented by the blocks 150 and 250 in FIG. 2, information relating to the individual's desired use of the apparatus is gathered by the device 10. This information relates on the one hand to the conditions of ergonomic and practical use of the apparatus (block 150) and the activities desired by the individual (block 160). This information is processed by the computing means to deduce therefrom on the one hand the ergonomic and practical characteristics of the apparatuses suitable for the questioned individual (block 160 of FIG. 2) and on the other hand the apparatuses suitable for these activities (block 260).

Finally, in step c2), the results of the first selection and of the processing of the information gathered about the conditions of use of the apparatus are compared in an analysis step (block 170), so as to select the apparatuses suitable for the use envisaged by the individual from among the apparatuses of the set exhibiting the optical characteristics liable to aid the individual (block 180).

In step c3), the results of the second selection and of the processing of the information gathered about the activities desired by the individual are compared in an analysis step (block 190), so as to select the apparatuses suitable for the activities envisaged by the individual from among the apparatuses of the second selection (block 200).

Step a)

In step a), at least one of the following characteristics of the vision of the partially-sighted person is determined: visual acuity, sensitivity to contrast, extent of the field of vision, glare, oculomotricity.

For this purpose, the computing means of the tablet are programmed to display on the screen 11 a series of tests making it possible to evaluate the characteristics of the individual's vision.

Each test comprises on the one hand the display of a sign on the screen and on the other hand, the reception of a signal emitted by the individual. The computing means of the tablet are programmed to interpret this signal and deduce therefrom the result of the test.

The signs displayed on the tablet correspond for example to a letter of an alphabet known to the individual or to a text drafted in a language spoken by the individual.

As explained in detail further on, the sequencing of the tests is determined by the computing means of the tablet as a function of the result of the earlier tests.

The tablet 10 being tactile, the signal emitted by the individual corresponds for example to the touching of a particular area of the tablet.

However, it is also possible to envisage other embodiments, in which the signal would be a sound signal emitted by the individual, for example when he reads a letter or a text on the tablet.

Hereinafter, an exemplary possible test will be described for various characteristics of the vision which can be evaluated. Other tests can obviously be envisaged and other characteristics of the vision can be tested.

Visual Acuity Test

The visual acuity test is for example carried out by displaying twelve lines of letters 20 as represented in FIG. 3. Each letter line is composed of five upper-case letters. The letters used are the letters called Sloan letters, that is to say S, O, C, D, K, V, R, H, N, Z, as is described in the work "Borish's Clinical Refraction", by William J. Benjamin, published in 2006 by Butterworth-Heinemann/Elsevier.

These letters are indeed easily recognizable. In a different language from French, and in particular in a language using a different alphabet, it is also possible to take all the letters of the alphabet or a different group of letters.

It is possible with the aid of a button displayed on the screen to distribute the letters over the screen in a random manner or in a predetermined manner so as to perform measurements of visual acuities under various conditions, for example under conditions of monocular or binocular vision, to perform a simple verification of acuity or in the case of several successive tests of one and the same individual. This makes it possible to avoid the memorizing of the tests by the individual.

In each line, the size of the letters corresponds to a visual angle of discrimination, that is to say to a determined visual acuity.

The size of the letters decreases from the first to the last line.

This signifies that if the individual succeeds in reading the letters of a given line, his visual acuity is greater than or equal to the visual angle of discrimination corresponding to the size of the letters of this line.

The size of the letters is for example calibrated for a reading distance of 40 cm. Here the visual acuity span tested depends in part on the resolution characteristics of the touchscreen used. It is possible with current screens to display lines of letters making it possible to test visual acuities lying between $5/10$ to $1/25$. Preferably, the visual acuity interval between each line is constant, thereby allowing regular and fine measurement whatever the tested span of visual acuities. In practice here, the letters of each line are taller than those of the line below by a constant multiplicative coefficient equal to the cube root of 2. The progression of the sizes of letters is thus logarithmic.

For a given line, the spacing between two letters is equal to the size of the letter of this line.

The spacing between two successive lines is equal to the size of the bottom line, that is to say the smallest size. The contrast of the displayed letters is 100%.

The individual must here point to the last line that he can read by touching the touchscreen at the level of this line. The tablet then records the visual acuity corresponding to this line as being the visual acuity of the individual.

For example, if the individual can read the fifth line of letters which measure 0.582 centimeters, but no line of letters situated below this fifth line, the computing means of the tablet deduce therefrom that the individual's visual acuity is $1/10$.

The vision aid apparatuses which will be able to aid the individual must then exhibit a magnification at least equal to 6.

This action furthermore brings about the following test.

Functional Acuity Test

The functional acuity test makes it possible to determine the wearers reading acuity and to obtain a more precise value of the useful magnification of the vision aid apparatus suitable for the individual.

The individual's vision characteristics related to the reading of a text depend on the individual's identification capabilities and oculomotricity capabilities in addition to his visual acuity.

If these capabilities are impaired, the magnification of the vision aid apparatus suitable for the individual will have to be increased accordingly.

The functional acuity test also makes it possible to determine the useful magnification of the vision aid apparatus under conditions closer to the individual's real life conditions.

In the exemplary functional acuity test described here, the computing means of the tablet are programmed to display on the screen a sentence consisting of 3 lines, therefore exhibiting two line wraps.

A line wrap can constitute difficulties for individuals whose vision is particularly degraded (loss of tags, skipping of lines, etc.).

The words of the selected sentences are preferably selected to be words that are simple to understand. These sentences originate for example from a well known text of the tale or fable type.

The component words of these sentences can also be chosen as a function of their occurrence in the language considered. These occurrences are determined by scientific studies.

These are preferably the most frequent words in the language considered.

Each sentence preferably comprises between 10 and 15 words exhibiting a homogeneous distribution of short words, comprising 2 letters or less, of words of average lengths, comprising between 3 and 5 letters and of long words, comprising more than 5 letters.

A single sentence is displayed centered on the screen 11. The size of the letters of the first sentence displayed after the visual acuity test, is a letter size corresponding to a lower acuity than that determined for the individual during the visual acuity test, that is to say to a larger letter size, to facilitate the reading of the first sentence.

The individual thereafter causes the display of other sentences with decreasing or increasing sizes of letters by touching the screen. The size of the letters of the sentences follows a logarithmic progression similar to that of the sizes of letters of the various lines of letters displayed during the visual acuity test.

The individual or the operator validates the sentence exhibiting the smallest size of letters for which reading is fluent and faultless.

The size of the letters of the validated sentence corresponds to a visual acuity which is the reading acuity. If this functional acuity is below the wearer's visual acuity, the smaller of the two values is retained by the computing means of the tablet.

Contrast Test

The contrast test makes it possible to measure the individual's sensitivity to contrasts. Contrast is defined as a capacity to be able to distinguish an object from its background. The contrast is defined as a % or a Log. It is for example calculated according to the Michelson contrast formula:

(LF−LO)/(LF+LO), where LF is the luminance of the background and LO the luminance of the object.

When the luminance is coded on one byte, the luminance of white is equal to 255 and the luminance of black is equal to 0.

A contrast of 100% corresponds to a black letter on a white background. The contrast test is performed in a recreational, simple and fast manner.

For this purpose, letters chosen from among the Sloan letters are displayed successively on the screen, on a white background. The letters exhibit a much greater size than the size corresponding to the visual acuity of the individual, for example a height of four centimeters.

For example letters exhibiting eight predefined contrasts are displayed, equal to the following values: 100%, 50%, 25%, 10%, 5%, 2.5%, 1.25%, and 0.6%. The displayed contrasts can also be chosen with a constant interval on a logarithmic scale.

The screen of the display is divided into 5 areas represented schematically in FIG. 4.

The quadrants 15, 16, 17, 18 correspond to the possible areas of display of the letter, here an H displayed in the top left quadrant. The area 19 is an area forming a response button "no letters perceived". The application displays a letter chosen randomly from among the Sloan letters in one of the quadrants 15, 16, 17, 18, also chosen randomly.

The contrast of the displayed letter decreases preferably progressively.

When he sees a displayed letter, the individual must read the letter out loud and touch the quadrant in which he sees the letter appear.

When the individual does not see any displayed letter, he has the possibility of indicating this by touching the area 19 of the screen.

The response is validated if the individual does indeed point to the letter displayed.

If the individual touches another area of the screen, the computing means consider that the individual has not perceived the letter displayed.

When a letter appears in a quadrant and the individual indicates that he does not see any letter or makes a mistake regarding the quadrant, this signifies that the maximum contrast perceived by the individual lies between the contrast values of the previous letter and of the displayed letter.

It is possible to envisage including in the series of displayed letters, every second letter displayed for example, a letter exhibiting a random contrast.

This renders the test more recreational and avoids making the individual blunder.

The computing means of the tablet record as contrast threshold the value of the contrast of the last letter seen. The contrast threshold is definitively validated when the individual has indicated the same contrast threshold three times to the computing means of the tablet.

Preferably, the first three letters displayed exhibit contrasts of 100%, 50% and 25% and are easily identifiable by the individual.

This constitutes a phase of training the individual and of giving them confidence. It makes it possible to verify that the individual has properly understood the operator's instructions. The results of this training phase are not taken into account in the calculation of sensitivity to contrasts.

Pointing Test

The pointing test makes it possible to characterize the quality of the individual's eye-hand coordination. Partially-sighted people may frequently exhibit defects of coordination which lead them to point alongside a targeted object. This characteristic related to the vision of the individual plays a significant role in the choice of vision aid apparatus.

For this test, the computing means are programmed to display black crosses on a white background, exhibiting a contrast of 100%, which are disposed in a random manner on the screen. The size of the cross is sufficiently large to remain visible to the individual as a function of the initially measured visual acuity.

If the visual acuity is less than or equal to 0.8/10, the size of the cross is equal to five centimeters.

If the visual acuity lies between 0.8/10 and 2.5/10, the size of the cross is equal to 3 centimeters.

If the visual acuity is greater than or equal to 2.5/10, the size of the cross is equal to 1.7 centimeters.

A pointing test comprises the displaying of a series of ten successive crosses on the screen. It is also possible to envisage displaying several series of crosses depending on whether one wishes to evaluate the coordination in monocular vision or in binocular vision.

The individual is then requested to point to the center of the cross displayed as quickly as possible. One logs, for each cross displayed, the time taken by the individual to point, equal to the time between the display of the cross and the moment at which the individual touches the screen and the pointing discrepancy between the center of the cross, with coordinates X_cross, Y_cross and the area of pointing of the finger, with coordinates X_finger, Y_finger.

After each pointing, a new cross is displayed on the screen at a random position.

For each test, the average of the discrepancy between the position of the center of the cross and the position of the point touched by the individual is defined.

An amplitude and a direction of the discrepancy are calculated.

A training phase can be added to the test. The latter then comprises the displaying of 13 crosses. The results of the first 3 trials are not counted.

Glare Test

The glare test makes it possible to determine the individual's sensitivity to light. The sensitivity is characterized by three parameters:
- the minimum luminous intensity measured in lux giving rise to an annoyance,
- the decline in visual acuity and in sensitivity to contrasts associated with this luminous intensity,
- the visual acuity recovery time and contrast sensitivity recovery time after prolonged exposure to light.

Accordingly the device consists of a display of letters of variable acuity and of variable contrast coupled to a light source. The light source comprises a dimmer making it possible to diffuse a luminous flux of between 0 and 7000 lux. The subject is situated between 40 and 60 centimeters from the luminous source. The luminous source can be either central and pointlike, or peripheral, for example annular or circular.

A set of letters is displayed initially, for example two or three letters, whose size and contrast allow the individual to clearly distinguish them in accordance with the results of the previous visual acuity and contrast tests.

The luminous flux diffused is thereafter increased progressively by the luminous source until the individual signals an annoyance.

A visual acuity test and a contrast test are then carried out again so as to determine whether there is a decrease in visual acuity and/or a loss of contrast.

If such is the case, the new visual acuity and the new perception of the contrast with this luminous flux are determined.

This step thus makes it possible to quantify the glare by determining the maximum luminous flux and the consequences of this luminous flux on the individual's vision.

In a second step, the individual is illuminated with a maximum luminous flux and the time required for the person to regain his initial visual acuity is measured.

This time called for example "recovery time", is measured either with a chronometer controlled by an operator or activated by a key on the tablet. The recovery time is then measured between the instant at which the individual touches the touchscreen of the tablet a first time, at the moment of the illumination and the instant at which the individual touches the screen again to indicate that he has recovered his visual acuity.

In practice, if this time is less than 30 seconds, it is not necessary to equip the individual with a filter. If this recovery time lies between 30 seconds and a minute it may be useful to suggest a filter for the individual and if the time is greater than a minute, it seems necessary to suggest a filter.

Other more precise examinations may be envisaged to confirm the necessity for a filter.

The result of the glare test makes it possible to determine the usefulness of the presence of a luminous filter integrated into the vision aid apparatus for limiting the glare and if appropriate to determine the characteristics of this filter.

Test of Extent of the Field of Vision

This entails determining whether the field of vision is limited by the presence of a "blind" area called scotoma, by a test of perimetric vision with a static or dynamic target, of variable shape and luminance levels.

This test is carried out by displaying a series of targets whose size and contrast are adjusted as a function of the result of the previous tests so that the individual can observe them without difficulty. The visual field describes a mapping of the patient's perception areas according to his luminous sensitivity.

The individual's field of vision is determined for example by testing each eye of this individual with a tablet whose dimensions are of the order of 20 centimeters wide and 30 centimeters long, disposed at a reading distance of 40 centimeters from the individual, and an angle at the vertex of the eye of +/−20 degrees. It is also possible to measure, for a tablet of given dimensions, the individual's maximum angle of vision, as is described for example in the document U.S. Pat. No. 7,549,743.

The analysis of the mapping and characteristics of the individual's visual field can be utilized to optimize the characteristics of the apparatus suggested to this individual, such as the field of vision of the apparatus, the need to strengthen contrasts, the addition of a filter and of extra lighting.

Oculomotricity Test

This test makes it possible to determine whether the wearer's eyes point with the same agility in all directions.

Accordingly, it is possible to use a text reading test or target tracking test.

The oculomotricity test also makes it possible to determine the stability of the ocular fixation. A target exhibiting for example the shape of a cross and of dimensions and contrasts suitable for the visual acuity of the wearer is displayed at the center of the screen. A camera records and follows the movements of the center of the eye, and more particularly the luminous corneal reflection caused by the presence of a point-like light, for example, a light-emitting diode, directed onto the eye according to a gaze tracking technique known per se.

The quality of the ocular fixation is evaluated by asking the person to fix on the cross center for 30 seconds. A camera records the variations in position of the corneal reflection during the test. Continuous or discontinuous movements of the eye are thus determined.

The measurement can be performed in monocular or binocular vision.

The evaluation of oculomotor quality has an impact in the choice of the aid, and more specifically concerning the visual field associated with the apparatus. A wearer with a high instability of ocular fixation will have better comfort and better performance with an apparatus exhibiting a large field of vision for the individual. An apparatus of the TV-magnifier type would for example in such a case be preferable to an apparatus of the Galilean system type since it exhibits a much more extensive field of vision.

Color Vision Test

The aim of the color vision test is to determine whether the individual's vision includes defects of perception of colors.

The test consists in ranking several patches of various colors according to three colorimetric axes. This ranking test is carried out by displaying patches of colors on the screen that the individual can move by touching the screen so as to rank them in the order of their tonality on the basis of a given color. Only the tonality of displayed patches varies, the saturation and the brightness of the patches are the same. Red/Green and Yellow/Blue dyschromatopsias can thus be detected.

The tests described previously are carried out one after the other. As explained previously, the first test carried out is the visual acuity test. The size of the signs displayed subsequently is thus determined as a function of the result of this test such that the individual can see the signs easily. Thereafter the reading acuity test, then the oculomotricity test, the pointing test, the contrast sensitivity test, the test of extent of the field of vision and the glare test are carried out, preferably in this order.

Step b)

In step b), the computing means determine at least one use, desired by the individual, of the group of at least one vision aid apparatus.

Desired use is intended to mean at one and the same time the activities that the individual desires to carry out with the apparatus and the desired ergonomic conditions of use of the apparatus.

In practice, in step b) it is determined whether at least one of the uses desired by the individual is desired:
  use in reading,
  use in writing,
  use for far vision,
  use for near vision,
  use for watching television,
  use for working on a screen situated at an intermediate distance.

Far vision for a partially-sighted person is intended to mean the viewing of an object situated at a distance from the individual of greater than or equal to 2 meters.

Near vision is intended to mean the viewing of an object situated at a distance from the individual lying between 30 and 50 centimeter, for example equal to 40 centimeters.

Intermediate distance is intended to mean an ergonomic on-screen working distance for the individual. This distance generally lies between 50 centimeters and a meter.

Accordingly, the device records, for each possible use taken into account by the computing means, an index of importance of this use for the individual. For example, the individual gives an index of importance of between 1 and 5 to each of the uses suggested hereinabove.

Preferably, in step b), at least one of the following ergonomic conditions of use desired by the individual for the envisaged uses is determined:
use outdoors,
use indoors,
use with the hands free,
use for a long duration.

Use for a long duration is intended to mean a use of greater than a few minutes, for example a use of greater than 30 minutes.

The device records, in a global manner for all the desired uses, the ergonomic characteristics desired for the vision aid apparatus. Accordingly the device records a binary ergonomic parameter, for example 1 or 0, + or −, indicating whether the ergonomic condition considered does or does not have to be fulfilled by the vision aid apparatus in order to satisfy the individual.

As a variant, it may be envisaged that the device records different ergonomic parameters for each use of the apparatus.

The device records for example whether or not the individual desires to keep their hands free. It also records whether the duration of use envisaged is long, for example to read a book for several hours, or whether it is short, for example to read the packaging of products in the supermarket.

Step c)

The computing means of the tablet comprise in memory a pre-established list of vision aid apparatuses.

These vision aid apparatuses are distributed into seven categories of vision aid apparatuses.

A first category comprises magnifying glasses.

The magnifying glass is a very simple product making it possible to enlarge a text or an object. The choice of a magnifying glass is a compromise between magnification and field of vision so as to offer a good reading speed.

There exist various types of magnifying glasses, among which for example:
pocket magnifying glasses for a short duration of use, both indoors and outdoors,
hand-held magnifying glasses for everyday use, short or long duration of use, both indoors and outdoors,
free-standing magnifying glasses which cause less fatigue, for longer duration of use and to keep the hands free,
illuminating magnifying glasses which ally magnification and strong contrast.

A second category contains microscopic spectacles. These spectacle are composed of a frame and of ophthalmic lenses with high powers, for example power of between +6 and +36 diopters.

A third category contains Galilean and Keplerian telescopic systems. These are devices intended to be mounted on a pair of spectacles. They are intended for near or far vision. They allow the partially-sighted person to perform all types of work while in most cases keeping their hands free.

These devices can exhibit a wide range of magnification and afford a wide field of vision.

Finally, for spot use, for example to read a street name, hand-held monocular devices will afford the necessary aid while remaining discreet.

A fourth category comprises portable electronic aids. Electronic aids exhibit very high magnifications and make it possible to improve the perception of contrasts. They are simple to use.

Portable electronic aids are lightweight and compact. They make it possible to afford considerable autonomy in everyday life.

Transportable electronic aids connect to all types of screens and can thus be moved around easily.

A fifth category comprises electronic aids of the TV-magnifier type.

A sixth category comprises lamps. Appropriate and good quality lighting appreciably increases visual acuity.

The various temperatures of colors available thus make it possible to define the most appropriate and most comfortable lighting. This optimization of the lighting makes it possible to reduce the magnification of the other aid apparatuses required.

Finally, the seventh category contains filters.

They allow an improvement in the perception of contrasts and a decrease in glare.

Like lamps, filters do not exhibit any magnification and can advantageously be allied with another vision aid apparatus.

Each vision aid apparatus is cataloged in a list in the form of an electronic register placed in memory in the computing means of the tablet.

Each record of this register comprises an identifier of the apparatus, first performance indices dependent on the aid afforded by this apparatus for all the possible vision characteristics of the individual and second performance indices dependent on the suitability of this apparatus for all possible uses.

The identifier of the vision aid apparatus corresponds for example to its name, to a manufacturer reference or to a code grouping together several items of information, for example manufacturer reference and category of vision aid to which it belongs.

Preferably, each record of the electronic register furthermore comprises an indicator of the ergonomic conditions of use of the corresponding apparatus.

The first and second indices of performance and the indicator of the ergonomic conditions of use are determined empirically during a phase of initializing the register. They can be modified on the basis of the experience of the user of the device, as a function in particular of the feedback given by individuals using the vision aid apparatuses.

The first indices of performance of the apparatus depend essentially on the optical characteristics of the apparatus, for example:
magnification of the apparatus,
capabilities for improving contrast,
extent of the field of vision with the apparatus,
possibility of use with a lamp or a filter,
fixed or variable, short or intermediate focusing distance,
depth of field of the apparatus.

In practice the first performance indices of each apparatus may for example comprise a first set of indices comprising all the possible magnifications of the apparatus. The record of the register corresponding to a vision aid apparatus possibly having a magnification of between 5 and 10 will thus comprise the first indices 5, 6, 7, 8, 9 and 10 for magnification.

These first indices also comprise a binary index indicating whether the apparatus is suitable for improving the perception of contrasts: electronic vision aid apparatuses are for example suitable for achieving this improvement, and will therefore have the index 1 for contrast improvement. These electronic vision aid apparatuses will also have an index 1 for magnification.

Optical apparatuses of the magnifying glass type not being suitable for improving contrast, they will have the index 0 for contrast improvement.

The second indices of performance of the apparatus depend on the technical characteristics described previously and on other practical characteristics of the apparatus, which render it more or less able to be used for a given use for example:

possibility of transporting the apparatus upon oneself, or on the contrary
possibility of fixing the apparatus on a fixed support,
possibility of fixing the apparatus on a pair of spectacles,
distance of use of the apparatus.

The second performance indices correspond for example to a score out of five values, for example varying from 0 to 4, of the performance of the apparatus for each use.

An illuminating free-standing magnifying glass will be particularly well suitable for be used for reading. Its performance index for reading will therefore be equal to four.

On the other hand, this magnifying glass will be ill-suitable for use for writing. Its performance index for writing will therefore be equal to 0.

Magnifying glasses not being suitable for far and intermediary vision, the second performance indices of this magnifying glass for the uses in far vision, for watching television and for working at an intermediate distance will be equal to 0.

The ergonomics-of-use indicator is here a binary indicator giving the suitability of the apparatus for certain conditions of use.

For example, a heavy hand-held apparatus will not for example be suitable for lengthy use. An apparatus allowing access to a very limited field of vision, or exhibiting a very small depth of field, and which is therefore difficult to maintain at its distance of use, will not be suitable for lengthy use. These apparatuses will have for example an indicator of value 0 for the suitability for long-duration use.

On the contrary, a vision aid apparatus that can be used at an ergonomic distance and that stands on a support permits longer-duration use and will have an indicator equal to 1 for this condition.

An apparatus having to be connected to the mains will not be suitable for outdoor use. Apparatuses of small size, lightweight and compact, such as certain magnifying glasses for example, which do not require any electrical power supply will be perfectly suitable for outdoor use.

For example, in the case of the magnifying glass described previously, assuming that the illuminating free-standing magnifying glass is of small size and battery-operated, the latter will be suitable for a short or long duration of use, since it can be stood and used outdoors.

According to the exemplary embodiment described here, the computing means are programmed to preselect, in the course of a first sorting, from among the pre-established list of vision aid apparatuses, that is to say from among the various records of the register, a set of vision aid apparatuses suitable for aiding the individual as a function of at least one characteristic of his vision determined in step a).

For example, the computing means select from the register solely the apparatuses suitable for providing the necessary magnification corresponding to the functional acuity determined previously by the reading acuity test.

If the functional acuity test has shown that the individual has a functional acuity of ¹⁄₁₀, the magnification of the suitable apparatus is equal to 6.

The first sorting then selects all the apparatuses whose first indices corresponding to the possible magnifications contain the value 6. These apparatuses form the set of apparatuses determined in step c1).

During a second sorting step, the computing means are here programmed to select, from among this set of vision aid apparatuses, a subset of vision aid apparatuses exhibiting the ergonomic conditions of use desired by the individual.

During this second sorting, the computing means here select the apparatuses whose indicators relating to the conditions of use correspond to the ergonomic parameters of the use desired by the individual.

For example, if the individual has indicated that he desired to use the apparatus over a long duration, indoors and with his hands free, the apparatus subset determined during the second sorting comprises all the apparatuses of the set determined in the first sorting that are able to be used under these conditions.

During a third sorting, the computing means of the device select from among the subset determined in the second sorting, the vision aid apparatuses at least one of whose second performance indices is greater than or equal to the index of importance assigned by the individual for the corresponding use.

For example, if the individual has assigned the index 4 to reading use, 2 to writing use and 0 to all the other uses, the third sorting selects the apparatuses whose second performance index for reading is equal to 4 and all those whose second performance index for writing is equal to 2, 3, or 4.

Finally, for each apparatus selected during the third sorting, the computing means determine a performance score as a function of the second performance indices of each apparatus for each use and as a function of the index of importance assigned to each use by the individual.

According to a first embodiment, the performance score is a global score obtained by summing the second indices of performance of each apparatus for all the uses whose index of importance for the individual is greater than a threshold value, for example greater than 2.

The device according to the invention then displays the apparatus group thus determined in the form of a list ranked as a function of this global score, for example according to decreasing global scores.

According to a second embodiment, the performance score determined is a weighted score reflecting in a more precise manner the fit between the performance of the apparatus for the possible uses of the apparatus and the importance of these uses for the individual.

For each of the envisaged uses, the computing means then calculate a ratio between the second performance index of the apparatus corresponding to this use and the index of importance of this use for the individual. The ratios of all the uses are thereafter summed to obtain the weighted score for the apparatus.

In practice, the device displays the list of the apparatuses thus determined ranked according to decreasing weighted scores. The device can also transmit the list determined to a computer.

As a variant, the device determines a single apparatus corresponding to the apparatus having the largest global or weighted score.

Many variants can be envisaged. The sequencing of the sorting steps can in particular be modified. It is for example possible to take into account firstly the uses envisaged by the individual before selecting the apparatuses exhibiting the ergonomic conditions requested by the individual. At each sorting step, the selection is performed from among the apparatuses selected at the previous step.

It is also possible to envisage any manner known to the person skilled in the art of determining a performance score for each apparatus: any type of average, weighted average etc.

Here, group of at least one apparatus is intended to mean a group comprising one or more apparatuses belonging to one or more categories of apparatus.

According to a simplified variant of the invention, it may be envisaged that the group of apparatuses that is determined by the device corresponds to one of the seven previously described categories of apparatuses. Accordingly, on completion of one of the previously described sortings, the device calculates a performance score associated with each category of apparatuses exhibiting apparatuses selected by the previous sorting. This category score is for example equal to the average over all the apparatuses of this category of the global scores or of the weighted scores described previously. The device then displays the category exhibiting the best score, or displays a ranking of the categories by decreasing scores.

As a variant, it is obviously possible to envisage that the device according to the invention consists of a non-tactile tablet, a computer or telephone screen or else that it comprises means for projection onto a screen. Provision may furthermore be made for the device to comprise means for adjusting the size of the signs displayed as a function of the distance of the individual in relation to the display screen.

Other types of vision test can be envisaged, as well as psychosensorial tests, for example to evaluate the perception of reliefs with stereoscopic tests, and this may have an influence on the choice of filter.

Tests to determine the individual's dominant eye, eye-head coordination or ergonomics tests of the apparatuses can also be carried out.

The results of these tests as well as the results of the tests of pointing, glare, field of vision, perception of colors and oculomotricity are taken into account by the computing means either in the course of the steps described previously, so as to refine the selection of the apparatuses by taking this information into account, or at the end of the selection process, so as to adjust the performance score of the apparatuses and make it possible to optimize their ranking.

This information can also be taken into account to determine whether it is opportune to supplement the apparatus selected by the previously described steps with a second apparatus of the filter or extra lighting type.

The invention claimed is:

1. A device for determining a group of at least one vision aid apparatus suitable for the vision of an individual, comprising:
   computing means with a memory, and in the memory, a pre-established list of vision aid apparatuses, programmed to:
   a) determine at least one characteristic of the vision of said individual,
   b) determine at least one use of the group of at least one vision aid apparatus, desired by the individual,
   c) determine said group of at least one vision aid apparatus as a function of the characteristic of the vision and of the use desired by the individual,
   said step c) comprising preselecting, in a course of a step c1), from among said pre-established list, a set of vision aid apparatuses suitable for aiding the individual as a function of at least one characteristic of the individual's vision determined in said step a).

2. The device as claimed in claim 1, in which, in step a), at least one of the following characteristics of the vision of the individual is determined: visual acuity, reading acuity, sensitivity to contrast, extent of the field of vision, glare, oculomotricity, eye-hand coordination, color vision, stereoscopy.

3. The device as claimed in claim 1, comprising a display part and in which, in step a), the characteristic of the vision of the individual is determined by virtue of a test of recognition of an image displayed on said display part.

4. The device as claimed in claim 3, in which, in step a), several characteristics of the vision of the individual are determined successively and in which the content or the sequencing of the subsequent tests of the vision is suitable as a function of the results of the previous tests.

5. The device as claimed in claim 1, in which, in step b), at least one of the following uses desired by the individual is determined: reading, writing, far vision, near vision, watching television, working on an object situated at an intermediate distance.

6. The device as claimed in claim 5, in which, in step b), at least one ergonomic condition desired by the individual for the desired use is recorded, from among the following ergonomic conditions: use indoors, use outdoors, standard ergonomic distance of use, long or short duration of use.

7. The device as claimed in claim 1, in which, in step b), the device records, for each desired use, an index of importance of this use for the individual.

8. The device as claimed in claim 7, in which, in step b), at least one ergonomic condition desired by the individual for the desired use is recorded, from among the following ergonomic conditions: use indoors, use outdoors, standard ergonomic distance of use, long or short duration of use.

9. The device as claimed in claim 1, in which, in step c), the computing means are programmed to select in a step c2), from among said set of vision aid apparatuses, a subset of vision aid apparatuses exhibiting the ergonomic conditions of use desired by the individual.

10. The device as claimed in claim 9, in which, in step c), the computing means are programmed to select in a step c3), from among said subset of vision aid apparatuses that is determined in step c2), a subset of vision aid apparatuses that is most suitable for the uses desired by the individual.

11. The device as claimed in claim 1, in which the list of vision aid apparatuses takes the form of an electronic register, each record of which comprises:
   an identifier of each vision aid apparatus,
   first performance indices dependent on the aid afforded by this apparatus for all the possible vision characteristics of the individual and
   second performance indices dependent on the suitability of this apparatus for all possible uses.

12. The device as claimed in claim 11, in which each record of the electronic register furthermore comprises an indicator of at least one ergonomic condition of use of the corresponding apparatus.

13. The device as claimed in claim 12, in which:
   in step c1), the computing means are programmed to preselect from said register the set of vision aid apparatuses for which at least one of said first indices corresponds to the associated vision characteristic of the individual,
   in step c2), the computing means are programmed to select from said set determined in step c1), the subset of vision aid apparatuses for which at least one indicator of the ergonomic conditions of use of the apparatus corresponds to the condition of use desired by the individual,
   in step c3), the computing means are programmed to select, from said set determined in step c2), the subset of vision aid apparatuses for which the second index is greater than a threshold value for at least one use desired by the individual.

14. The device as claimed in o claim 1, suitable for the determination of a group of at least one vision aid apparatus for a partially sighted individual.

* * * * *